United States Patent [19]
Kennedy

[11] Patent Number: 5,975,901
[45] Date of Patent: Nov. 2, 1999

[54] DENTAL PEN PIC

[76] Inventor: Joseph H. Kennedy, P.O. Box 66251, Scotts Valley, Calif. 95067

[21] Appl. No.: 09/306,839

[22] Filed: May 7, 1999

[51] Int. Cl.[6] .............................. A61C 15/00; A61C 3/00; B65D 65/28; A24F 15/04

[52] U.S. Cl. ......................... 433/141; 132/321; 132/309; 206/380; 221/24

[58] Field of Search ............................. 433/141; 221/34, 221/67, 92, 68, 24; 206/380; 604/195; 132/321, 317, 318, 314, 297, 309

[56] References Cited

U.S. PATENT DOCUMENTS

| | | | |
|---|---|---|---|
| 505,823 | 10/1893 | Faber | 206/380 |
| 2,360,765 | 10/1944 | Davidson | 206/380 |
| 4,269,313 | 5/1981 | Smith | 206/380 |
| 5,009,535 | 4/1991 | Oilar | 401/195 |
| 5,855,215 | 1/1999 | Clarke | 132/321 |
| 5,881,742 | 3/1999 | Hunsberger | 132/297 |

*Primary Examiner*—John J. Wilson
*Assistant Examiner*—Robyn Doan
*Attorney, Agent, or Firm*—John B. Dickman, III

[57] ABSTRACT

A combination toothpick holder and toothpick which is formed of a tube having cylindrical openings in which a plurality of toothpick ends are inserted, stored and used. The toothpick holder inside diameter is such to frictionally grip the toothpick ends and hold them in place both in the holder and in the ready to use position. The toothpick ends are made of a reusable plastic material and are provided with pointed ends especially configured for cleaning teeth.

6 Claims, 3 Drawing Sheets

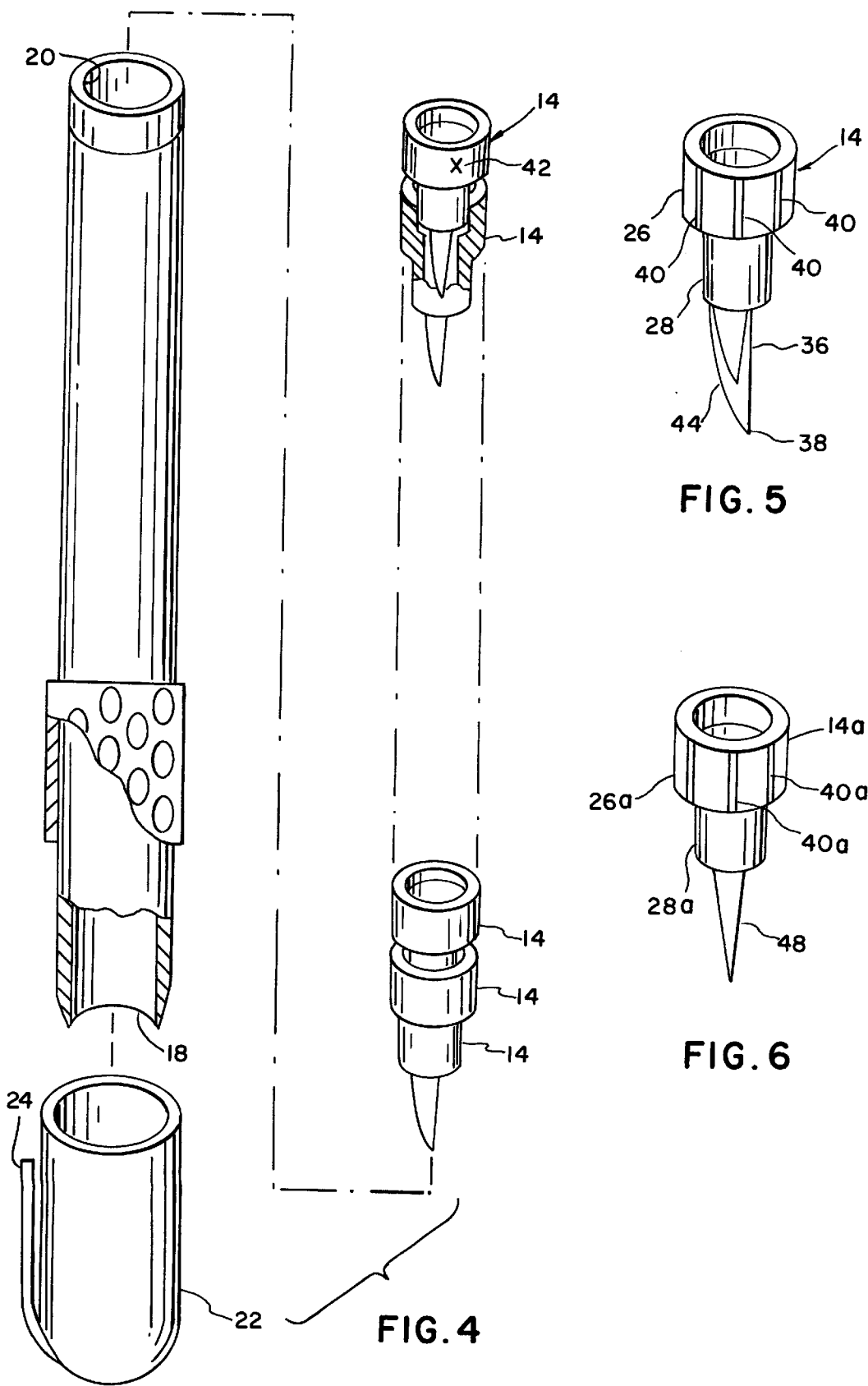

DENTAL PEN PIC

BACKGROUND OF THE INVENTION

The present invention relates to reusable toothpicks, and in particular to a combination toothpick holder and reusable toothpicks dispensed from the holder.

Prior toothpicks have taken many shapes and have been composed of many materials. Wooden toothpicks, for example, may have a single pointed end and a flat end with an arcuate shape, or both ends may be pointed. Plastic toothpicks may be shaped like the described wooden toothpicks or they may be of tubular shape with diagonally sharpened ends.

There are inherent problems with the prior art toothpicks, wooden toothpicks can break or splinter, resulting in possible mouth or finger damage. On the other hand, plastic toothpicks can be very hard which if improperly used can cause tooth or gum damage. Another problem exists with both wooden or plastic toothpicks, if they are not immediately disposed of, they may be reused. Reusing such toothpicks can cause sanitary health issues.

Heretofore, there has not been a toothpick holder for storing and dispensing toothpick ends. In fact, to the inventor's knowledge, there is only U.S. Pat. No. 579,139, issued to DEARDORFF, which shows a replaceable toothpick in a holder, with a recess for housing the toothpick and supporting it in a use position. There are multiple holders with a cavity to house a tool implement or plurals of the same. One example is U.S. Pat. No. 5,388,698, issued to WAKAO, which is directed to a carrier/dispenser for dispensing capsules.

BRIEF SUMMARY OF THE INVENTION

This invention is directed to a combination toothpick holder and toothpick where a length of rigid cylindrical tubing is adapted to receive and dispense toothpick ends. The toothpick holder also serves as a handle for a toothpick end for cleaning between teeth and gums. Each toothpick end has a cylindrical base of a diameter to just slide inside the toothpick holder. The cylindrical base is integral with an end that is either a sword type or a pointed type. The cylindrical base has a plurality of protuberances for creating a snug, slip fit with the toothpick holder to hold the toothpick ends within the holder and to secure an exposed toothpick in the use position.

It is therefore an object of this invention to provide a combination toothpick holder/handle and toothpick end where the toothpick holder/handle will contain and store a plurality of said ends.

It is another object of this invention to provide a combination toothpick holder/handle and toothpick end which is easily manufactured.

Another object of this invention is to provide a combination toothpick holder/handle and toothpick ends where the toothpick ends are stored in a clean sanitary holder.

Still a further object of this invention is to provide a marker toothpick end to indicate when all of the stored ends have been used.

In accordance with these and other objects which will become apparent herein, the present invention will now be described with reference to the accompanying drawings.

BRIEF DESCRIPTION OF THE DRAWINGS

FIG. 4 is a disassembled view of the invention showing a holder/handle, a removable cap and a plurality of toothpick ends.

FIG. 5 is a perspective view of a toothpick end of the invention.

FIG. 6 is a perspective view of another embodiment of a toothpick end of the invention.

DETAILED DESCRIPTION OF THE INVENTION

Figure 7:
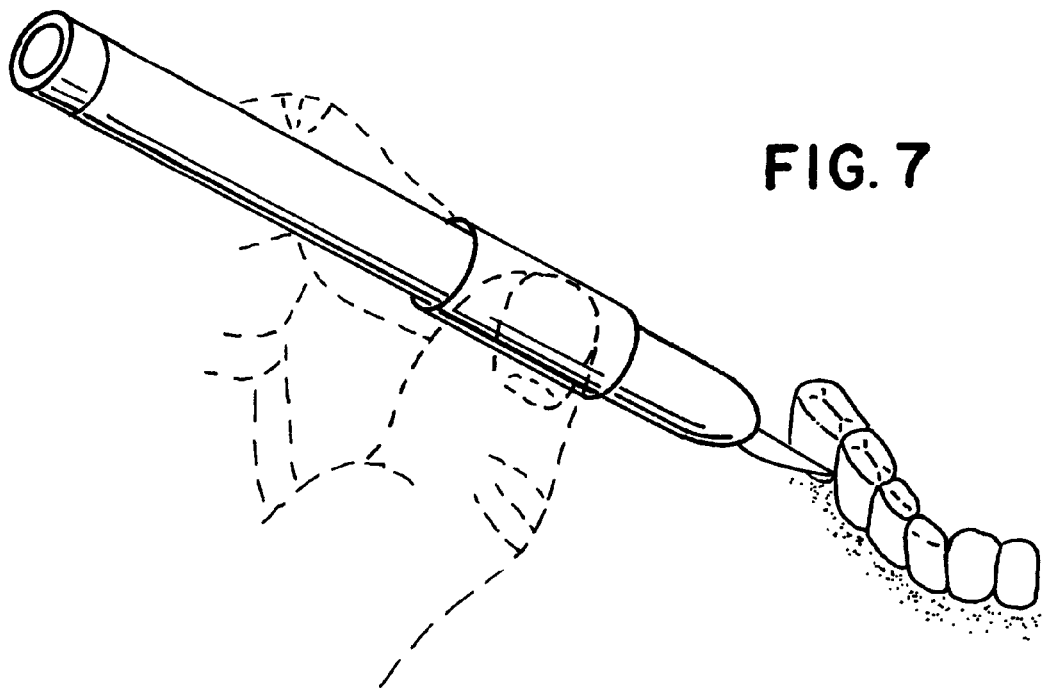
FIG. 7 is a perspective view of a combination toothpick holder/handle and toothpick end in use on the outside area of teeth and gums.
Figure 8:
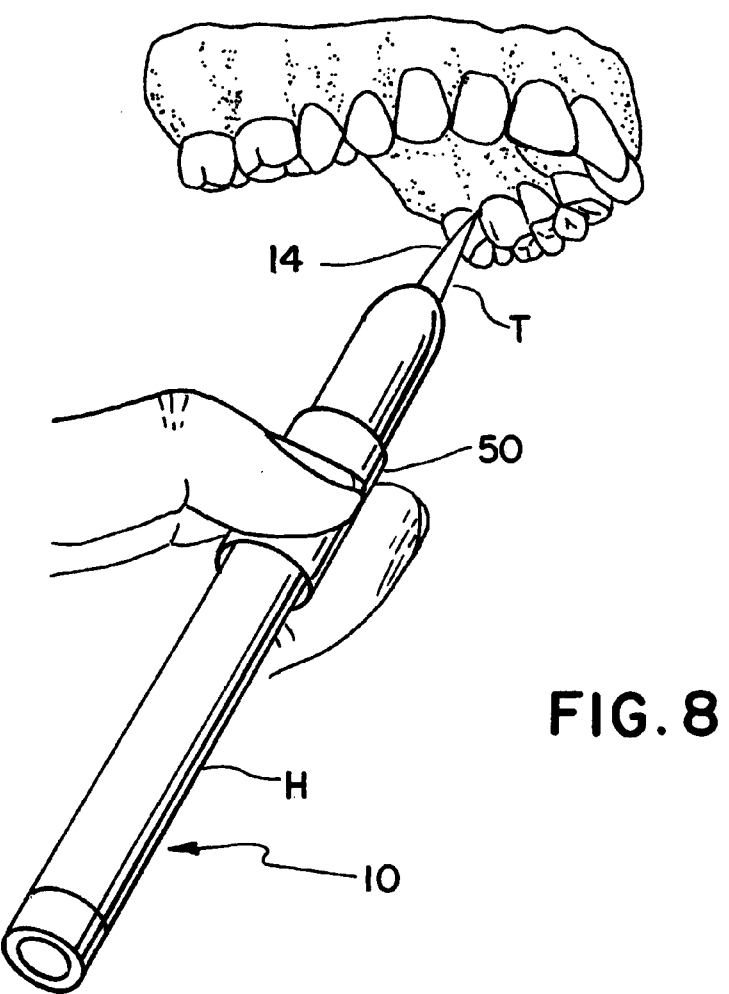
FIG. 8 is a perspective view of the device in use on the inside of the teeth and gums.

Referring to the drawings, FIGS. 1–8, there is shown a combination toothpick holder/handle and toothpick ends 10 for cleaning between teeth and gums as shown in FIGS. 7 and 8. The combination toothpick holder/handle, hereafter referred to as toothpick handle 12, and toothpick ends, hereafter referred to as toothpick 14, 10 provides multiple toothpicks 14 housed in toothpick handle 12. Toothpick handle 12 is a cylindrical tube 16 that is open on each end 18 and 20 to receive and support toothpicks 14. A cap 22 covers one or the other end 18 or 20, and includes a pocket clip 24. The toothpick handle 12 and cap 22 are molded from a rigid plastic, such as polystyrene, or other suitable plastics.

Figure 1:
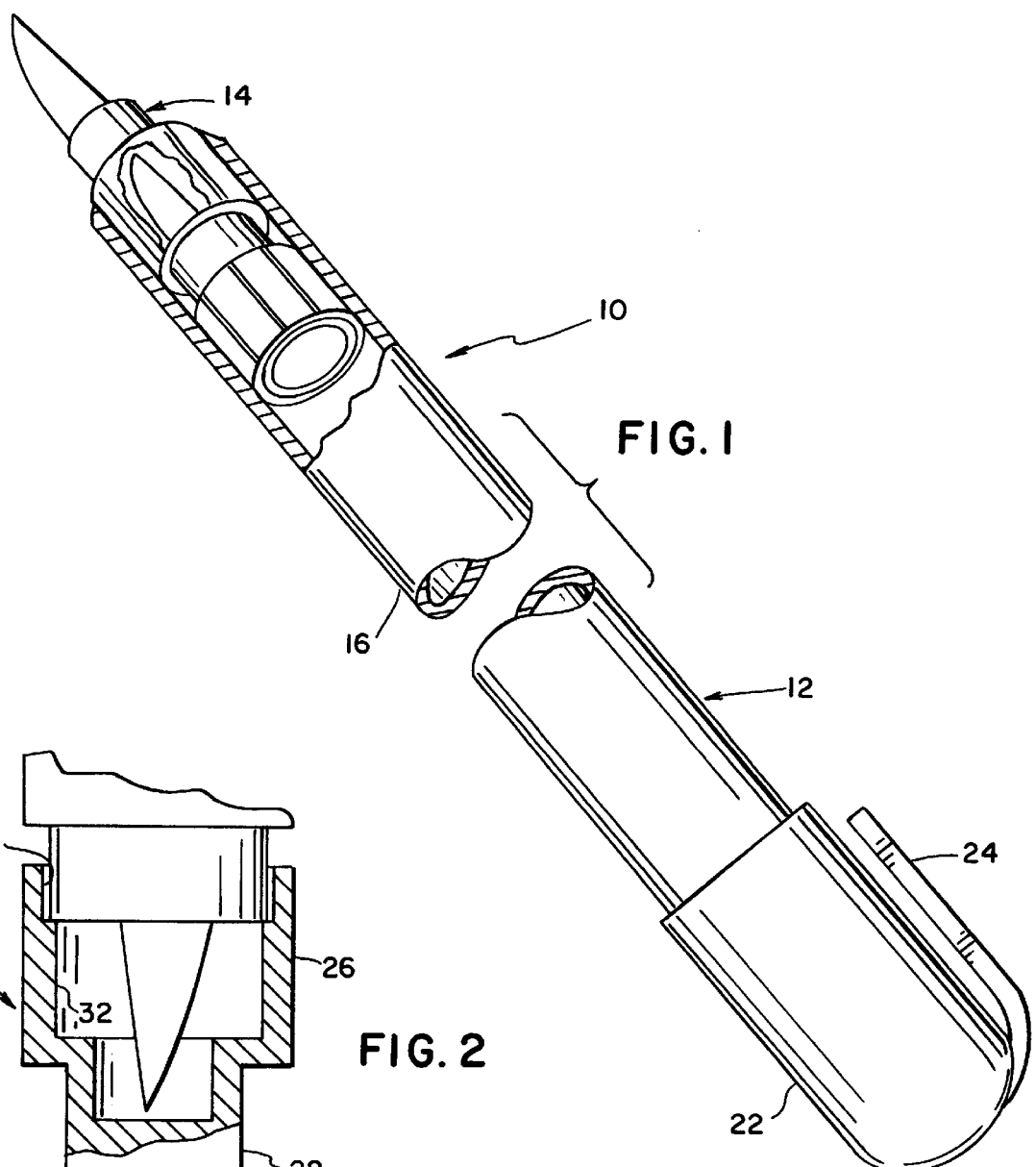
FIG. 1 is a side elevation of a combination toothpick holder/handle and toothpick ends with a partial cutaway view showing a plurality of toothpick ends and how they fit within each other.
Figure 2:
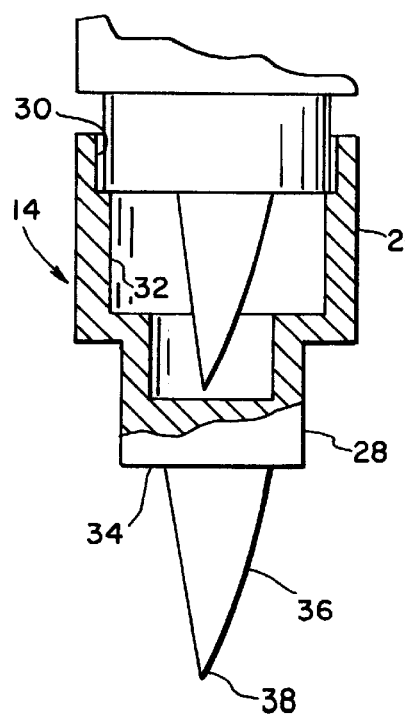
FIG. 2 is an exploded view of multiple toothpick ends with a partial cross-section of one of the ends.

The toothpick 14, FIG. 2, is molded of a polypropylene and polyethylene to provide the desired firmness and pliability for loosening debris and plaque. Other suitable molding materials may be used just to provide firmness and pliability necessary for cleaning between teeth and gums. Each toothpick 14 has a hollow cylindrical base 26 integrally molded with a tip support 28 which is also hollow and cylindrical. Base 26 is larger than tip support 28 so that a plurality of toothpicks 14 can be stacked one in another. Base 26 has groove 30 on the inside wall 32 for the exterior end 34 of support 28 to rest upon. Toothpick tip 36 is integrally molded in exterior end 34, with a pointed tip 38 for proper cleaning.

Figure 3:
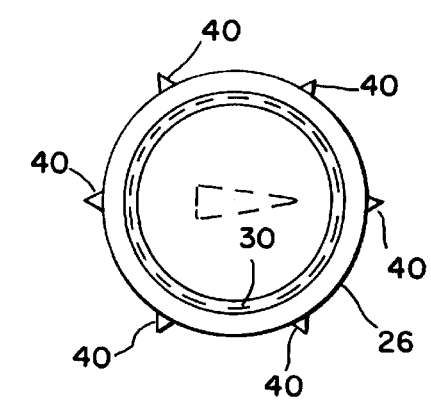
FIG. 3 is a top view of a toothpick end of the invention.

FIG. 3 shows base 26 and groove 30, and a plurality of protuberances 40. When each toothpick 14 is slid into toothpick handle 12, the protuberances 40 frictionally engage the inside of handle cylinder 16 to hold each toothpick 40 in place. After a toothpick 14 is used, it is removed from end 18 and reinserted in end 20. When all of the toothpicks 14 have been used, they are removed from handle 12, cleaned and reinserted, or completely replace with a new unused refill package of toothpicks. In order to determine when the last clean toothpick 14 has been used, it will have an identifying mark, as shown in FIG. 4, where the top most toothpick 14 has an identifying mark 42 "X". Instead of an identifying mark 42, the toothpick can be a different color to stand out as the last one.

The toothpick 14, FIG. 5 has a blade or sword-like end 36, that has an edge 44 and pointed end 38. This type of end is especially designed for cleaning between teeth, while the pointed end 38 is serviceable for cleaning the gum area.

The toothpick end embodiment of FIG. 6 is particularly designed to clean and stimulate the gums. Toothpick 14a has a pointed cone shaped end 48. The cone shaped end 48 will clean the area along the gum where it contacts the teeth.

Another feature of the toothpick handle is a sleeve 50 to be gripped by the user as shown in FIG. 8.

While the present structures have been described and shown, it is conceived that other embodiments may be realized, therefore, for a complete understanding of the invention, the drawings and description should be considered in accordance with the following claims.

What is claimed:

1. A combination toothpick holder/handle and toothpick ends comprising:

a hollow cylindrical tube for holding toothpick ends and a handle for an exposed toothpick end;

said hollow cylindrical tube holds a plurality of toothpick ends and is of a rigid construction to resist bending;

a toothpick end having a base and a pointed end for cleaning between teeth and gums;

said toothpick end base having a cylindrical shape of a diameter to slide within said cylindrical tube, said base is in frictional contact with said cylindrical tube; and, said base is molded with a tip end support and a tip; where said base and said tip end support are hollow, with said base having an open end and a groove within said open end to receive and support a toothpick end so that said toothpick ends are stackable for inserting in said hollow cylindrical tube.

2. A combination toothpick holder/handle and toothpick ends as in claim 1 wherein said hollow cylindrical tube comprises a rigid plastic.

3. A combination toothpick holder/handle and toothpick ends as in claim 2 wherein said hollow cylindrical tube has a gripping sleeve.

4. A combination toothpick holder/handle and toothpick ends as in claim 3 wherein said toothpick end base has a plurality of protuberances for frictionally engaging the inside of said hollow cylindrical tube to hold said toothpick ends in place.

5. A combination toothpick holder/handle and toothpick ends as in claim 4 wherein said toothpick tip end has a blade-like tip.

6. A combination toothpick holder/handle and toothpick ends as in claim 4 wherein said toothpick tip end has a conical shape for cleaning between teeth and gums.

* * * * *